United States Patent [19]

Mercer et al.

[11] Patent Number: 5,235,044
[45] Date of Patent: Aug. 10, 1993

[54] COMPOUNDS HAVING OXADIAZOLE AND TRIAZENE MOIETIES, CROSSLINKABLE POLYMERS THEREFROM, AND METHODS THEREFOR

[75] Inventors: Frank W. Mercer, Belmont; Aldrich N. K. Lau, Palo Alto; Lanchi P. Vo, San Jose, all of Calif.

[73] Assignee: Raychem Corporation, Menlo Park, Calif.

[21] Appl. No.: 943,370

[22] Filed: Sep. 9, 1992

[51] Int. Cl.$^5$ ............... C07D 271/107; C08L 71/12
[52] U.S. Cl. ........................... 534/551; 534/550
[58] Field of Search ................... 534/550, 551

[56] References Cited

FOREIGN PATENT DOCUMENTS

| | | |
|---|---|---|
| WO91/09070 | 6/1991 | World Int. Prop. O. |
| WO91/09071 | 6/1991 | World Int. Prop. O. |
| WO91/09081 | 6/1991 | World Int. Prop. O. |
| WO91/09087 | 6/1991 | World Int. Prop. O. |
| WO91/16369 | 10/1991 | World Int. Prop. O. |
| WO91/16370 | 10/1991 | World Int. Prop. O. |

OTHER PUBLICATIONS

Hedrick, Polym. Bull., 25(5), 543-550 (1991).

*Primary Examiner*—Mary C. Lee
*Assistant Examiner*—Fiona T. Powers
*Attorney, Agent, or Firm*—Herbert G. Burkard; Yuan Chao

[57] ABSTRACT

A composition having the structure

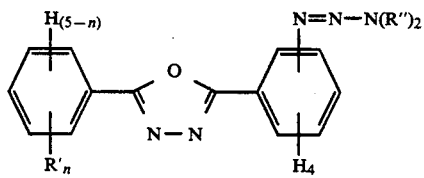

wherein —R' is —F or —Cl, each —R", which may be the same or different, is independently selected from the group consisting of $C_1$-$C_6$ alkyl or hydroxyalkyl moieties and aryl moieties, and n is 1 or 2. These compositions are useful as co-monomers or end-cappers for the introduction of thermally reactive cross-linking sites into polymers.

12 Claims, No Drawings

COMPOUNDS HAVING OXADIAZOLE AND TRIAZENE MOIETIES, CROSSLINKABLE POLYMERS THEREFROM, AND METHODS THEREFOR

TECHNICAL FIELD OF THE INVENTION

This invention relates to compounds having oxadiazole and triazene moieties, crosslinkable polymer compositions made from such compounds and methods for making the same.

BACKGROUND OF THE INVENTION

It has been proposed to use fluorinated poly(arylene ethers) for electronic applications, such as insulators or passivation layers in multilayer integrated circuit devices or multichip modules. Mercer, WO 91/09070 (1991); Mercer et al., WO 91/16369 (1991). Their advantages include chemical inertness, low dielectric constant, insensitivity to ambient humidity, and ease of coating over a substrate.

Fluorinated poly(arylene ethers) may be crosslinked to improve solvent resistance and/or help preserve mechanical properties at elevated temperatures. Bis-triazene crosslinking agents whose triazene groups decompose upon heating and form reactive crosslinking sites have been used. Lau et al., WO 91/09087 (1991); Mercer et al., WO 91/09081 (1991) and WO 91/09071 (1991). It has also been proposed to use oligomers which are crosslinkable via reactive terminal groups. Mercer et al., WO 91/16370 (1991). Copending, commonly assigned U.S. application Ser. No. 07/943,093, filed even date herewith, discloses the crosslinking of fluorinated poly(arylene ethers) with 1-[(hydroxyphenoxy)]phenylenetriazenes.

Other polymers, such as poly(ether ketones), poly(sulfones), and poly(ether imides), can also benefit from crosslinking, either to improve high temperature mechanical properties or solvent resistance.

Also of interest is Hedrick, Polym. Bull. 25 (5), 543–550 (1991), which discloses the synthesis of poly(aryl ether oxadiazoles) which are melt or solution processable.

We have discovered new compounds which are utilizable as comonomer or end-cappers for the preparation of many polymers and which contain a thermally reactive crosslinking site.

SUMMARY OF THE INVENTION

This invention provides a composition having the structure

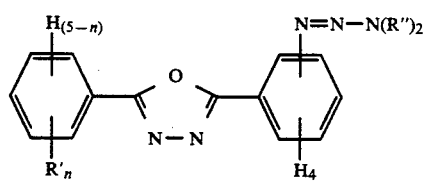

wherein —R' is —F or —Cl, each —R", which may be the same or different, is independently selected from the group consisting of C$_1$-C$_6$ alkyl or hydroxyalkyl moieties and aryl moieties, and n is 1 or 2.

This invention also provides a crosslinkable polymeric composition comprising a polymer having (a) repeat units of the structure -W-Ar-, where -W- and -Ar- are mononuclear or polynuclear aromatic moieties, and (b) further having a plurality of crosslinking sites selected from the group consisting of (i) a co-repeat unit

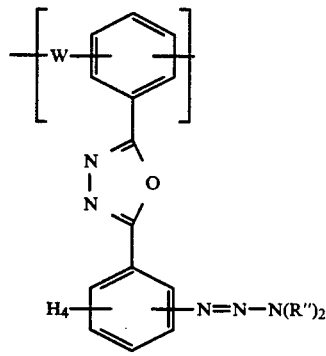

and (ii) an end group

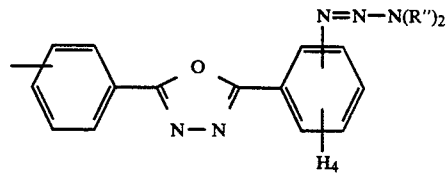

wherein —R" is as defined above. The degree of polymerization is preferably between 6 and 100, more preferably between 6 and 50.

Another embodiment of the invention provides a method of making a crosslinkable polymeric composition, comprising reacting a diphenol monomer H-W-H with an aromatic dihalide Hal-Ar-Hal, where -W- is the residuum of a dihydric phenol, -Ar- is a divalent mononuclear or polynuclear aromatic moiety, and -Hal is halogen, in the presence of a compound of the structure

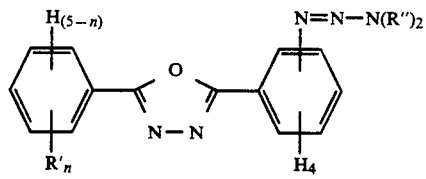

wherein —R' and —R" are as defined above.

DESCRIPTION OF THE PREFERRED EMBODIMENTS

Compounds I of this invention

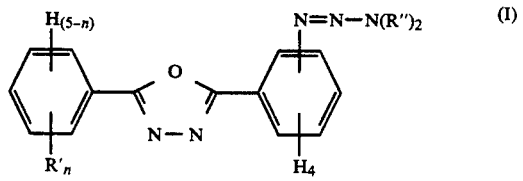

can be prepared as follows (where n, —R', and —R" are as previously defined):

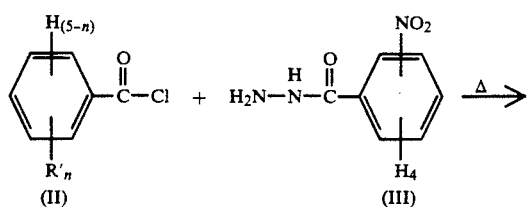

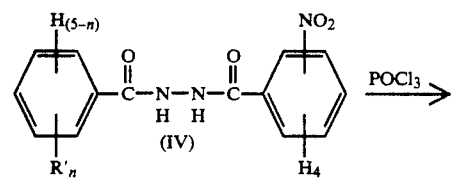

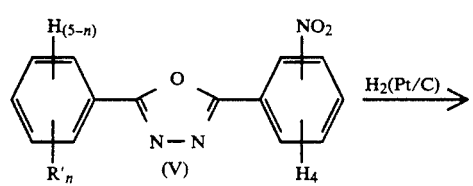

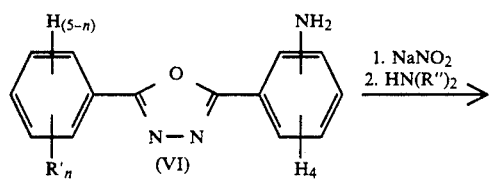

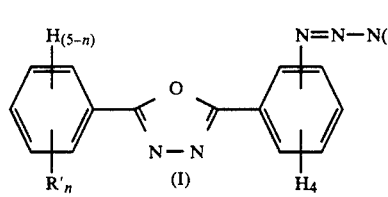

For convenience of reference, in compound I the ring positions of the —R' bearing ring are identified by the numerals 2 through 6, while the ring positions in the triazene bearing ring are identified by the numerals 2' through 6':

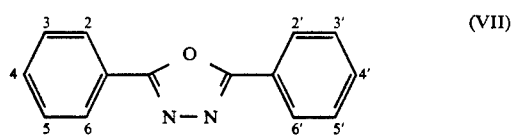

Preferred positions for the —R' group are 2,4- or 2,6-(where n is 2) and 4 (where n is 1). Preferably, —R' is —F. Preferred positions for the triazene moiety are 4' or 3'. Preferably, each —R" is the same and is selected from the group consisting of —CH$_3$, —CH$_2$CH$_3$, —CH$_2$CH$_2$CH$_2$CH$_3$, and —CH$_2$CH$_2$OH; more preferably, each —R" is methyl. In an alternative preferred embodiment, at least one —R" is phenyl. Preferred compounds I are shown below:

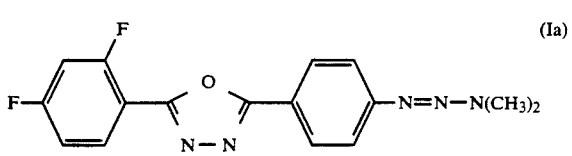

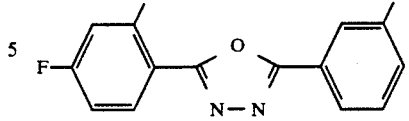

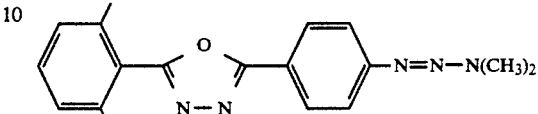

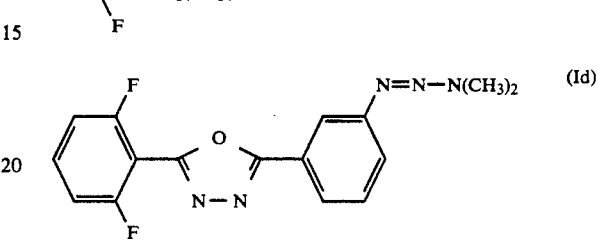

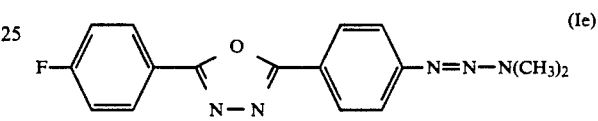

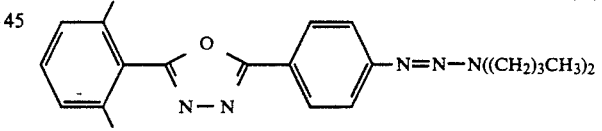

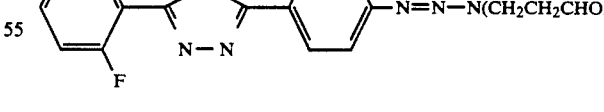

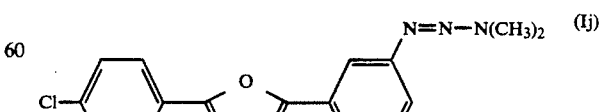

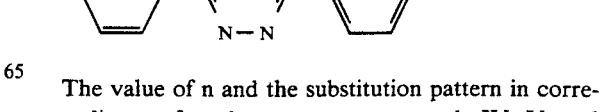

The value of n and the substitution pattern in corresponding preferred precursor compounds IV, V, and VI are provided in Table I:

TABLE I

Preferred Compounds IV, V, and VI

| Compounds | n | R' | Nitro or amino position |
| --- | --- | --- | --- |
| IVa, Va, or VIa | 2 | 2,4-F | 4' |
| IVb, Vb, or VIb | 2 | 2,4-F | 3' |
| IVc, Vc, or VIc | 2 | 2,6-F | 4' |
| IVd, Vd, or VId | 2 | 2,6-F | 3' |
| IVe, Ve, or VIe | 1 | 4-F | 4' |
| IVf, Vf, or VIf | 1 | 4-F | 3' |
| IVj, Vj, or VIj | 1 | 4-Cl | 3' |

Compounds I can be used as co-monomers in nucleophilic polymerizations, in which a diphenol monomer H-W-H reacts with an aromatic dihalide monomer Hal-Ar-Hal to form a polymer having a repeat unit -W-Ar-:

H—W—H+Hal—Ar—Hal→—W—Ar—+2H.Hal

—W— is the residuum of a dihydric phenol and —Ar— is a divalent mononuclear or polynuclear aromatic moiety and Hal is a halogen (preferably fluorine or chlorine activated towards nucleophilic displacement by an electron withdrawing substituent such as sulfone or ketone in the aromatic ring to which Hal is bonded).

Nucleophilic polymerizations can be used to make a variety of polymers, including poly(arylene ether ketones), poly(arylene ether sulfones), and fluorinated poly(arylene ethers). Replacement of some of the Hal-Ar-Hal monomer with an equivalent amount of compound I (where n is 2) leads to the formation co-repeat units VIII

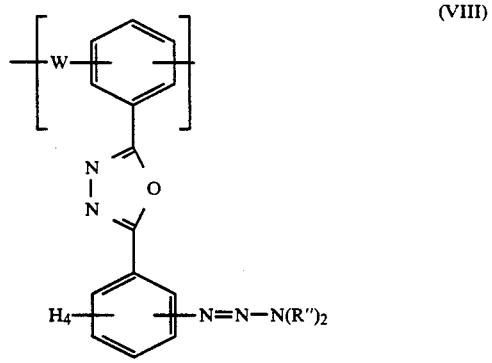

(VIII)

Co-repeat units VIII can serve as sites for crosslinking the main polymer -W-Ar-. It is believed that, when heated up to or above a threshold temperature, the triazene groups decompose to form phenyl radicals or other reactive centers. These then insert into aromatic groups in the polymer to form aryl-aryl crosslinkages, as discussed in Lau et al., WO 91/09087 (1991), the disclosure of which is incorporated herein by reference.

Where n equals 1, compound I can be used as an end-capping reactant to form polymers or oligomers having a repeat unit -W-Ar- and end groups of the structure IX:

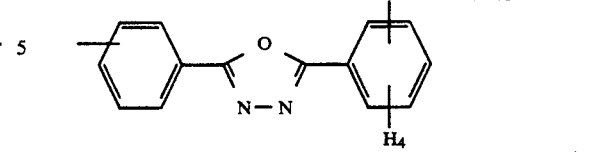

(IX)

Upon heating the terminal triazene groups decompose as discussed above to form reactive crosslinking sites. To ensure complete double-capping, an excess of diphenol H-W-H is used over dihalide Hal-Ar-Hal during polymerization, such that the total molar amount of diphenol equals the amount of Hal-Ar-Hal plus compound I.

If desirable, a combination of both co-repeat units VIII and end groups IX can be used.

The monomers are used in substantially stoichiometric amounts if high molecular weight polymer is desired. Alternatively, if lower molecular weight material is desired, for example to facilitate the preparation of solutions for spin or other solvent coating operations, a slight stoichiometric excess of either monomer can be used to control the molecular weight. The amount of compounds I to be used, either as comonomers or end-cappers, is preferably between about 2 and about 15 mole %, more preferably between about 2 and about 10 mole %.

The use of compounds I to provide crosslinking sites has several advantages over the prior art. The triazene group is thermally more stable than conventional non-triazene crosslinking agents such as peroxides and are therefore less susceptible to premature decomposition. The instant triazene systems are copolymerized to form a one-component system, alleviating any concerns about phase separation and/or compatibility, as might be found in non-copolymerized triazene systems such as disclosed in Lau et al., WO 91/09087 (1991); Mercer et al., WO 91/09081 (1991) and WO 91/09071 (1991). Further, we have unexpectedly discovered that the instant compounds are effective crosslinkers, providing a high degree of crosslinking (as measured by gel content) even when used in relatively low molar amounts.

Among the polymers which can be crosslinked by incorporation of a selected molar amount of either co-repeat units VIII or end groups IX are the fluorinated poly(arylene ethers) X having a repeat unit of the structure

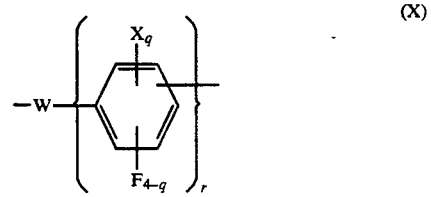

(X)

wherein —W— is

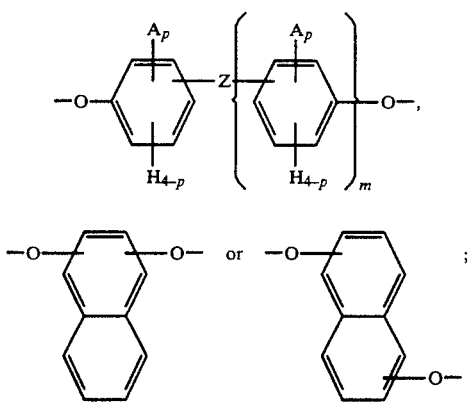

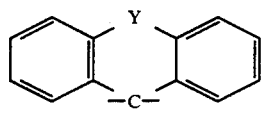

wherein each —A is independently —F, —Cl, —Br, —CF₃, —CH₃, —CH₂CH=CH₂, or —C₆H₅; p is 0, 1, or 2; —Z— is a direct bond, —C(CH₃)₂—, —C(CF₃)₂—, —O—, —S—, —SO₂—, —CO—, —P(C₆H₅)—, —C(CH₃)(C₆H₅)—, —C(C₆H₅)₂—, —(CF₂)$_{1-6}$—, or

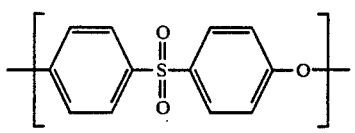

wherein —Y— is —O— or a direct bond; and m is 0, 1, or 2;
each —X is independently —H, —Cl, —Br, —CF₃, —CH₃, —CH₂CH=CH₂, or —C₆H₅;
q is 0, 1, or 2; and
r is 1 or 2.

Fluorinated poly(arylene ethers) X can be prepared by the polymerization of a diphenol H-W-H with a fluorinated monomer XI

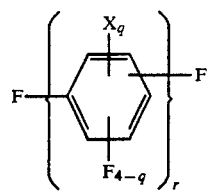

(XI)

where —X, q, and r are as previously defined.

Suitable diphenols H-W-H include 4,4'-(hexafluoroisopropylidene)diphenol (also known as Bisphenol AF), 4,4'-isopropylidene-di(2,6-dimethylphenol), 4,4'-(1-phenylethylidene) bisphenol, 4,4'-isopropylidenediphenol (also known as Disphenol A), 9,9'-bis(4-hydroxyphenyl)fluorene, 1,5-dihydroxynaphthalene, 2,7-dihydroxynaphthalene, resorcinol, and 4,6-dichlororesorcinol. Preferred ones include 4,4'-(hexafluoroisopropylidene)diphenol, 9,9'-bis(4-hydroxyphenyl)fluorene, and 1,5-dihydroxynaphthalene.

Suitable fluorinated monomers XI include hexafluorobenzene, decafluorobiphenyl, pentafluorobenzene, octafluorotoluene, 1,4-dibromotetrafluorobenzene, chloropentafluorobenzene, allylpentafluorobenzene, and 2,2',3,3',5,5',6,6'-octafluorobiphenyl.

A base such as an alkali metal carbonate, bicarbonate, or hydroxide is added to the polymerization mixture to convert the phenoxy groups to the corresponding phenoxides. Sodium and potassium carbonate are preferred. A polar aprotic solvent, such as N,N-dimethylacetamide (DMAc), N,N-dimethylformamide (DMF), or 1-methyl-2-pyrrolidinone (NMP) is used. The reaction is carried out at an elevated temperature, although such temperature should not be excessively high. A temperature between about 50° C. and about 125° C. is generally suitable, with a temperature between about 60° and about 90° C. being especially preferred. Reaction times are typically between about 10 and about 72 hours. The preparation of fluorinated poly(arylene ethers) X is further described in allowed copending, commonly assigned U.S. application of Mercer et al., U.S. Ser. No. 07/583,897, filed Sep. 17, 1990, and in Mercer et al., U.S. Pat. Nos. 5,114,780 (1992) and 5,115,082 (1992), the disclosures of which are incorporated herein by reference.

Another class of polymers into which can be crosslinked by the incorporation of corepeat units VIII or end groups IX are the poly(arylene ether sulfones) XII, including those having repeat units XIIa-d:

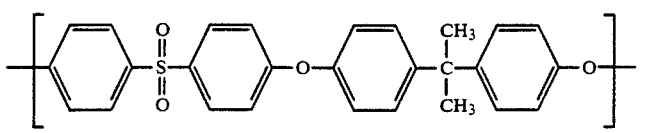

(XIIa)

(XIIb)

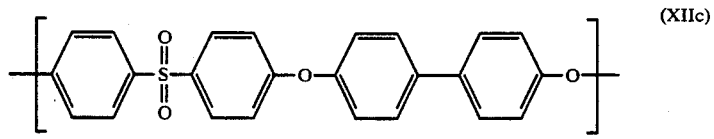

(XIIc)

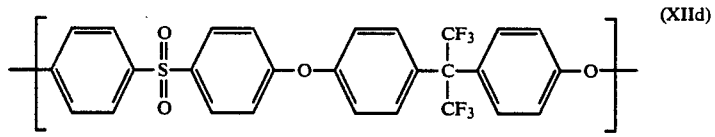

(XIId)

The poly(arylene ether sulfones) can be made from the polymerization of a diphenol H-W-H with an aromatic dihalide compound having halogens (preferably chlorine or fluorine) activated towards nucleophilic substitution, at least one of the diphenol and the dihalide compound having a sulfone group. Suitable dihalide compounds include 4,4'-difluoro- and 4,4'-dichlorobenzophenone and 4,4'-difluoro- and 4,4'-dichlorodiphenyl sulfone. Suitable diphenols H-W-H include 4,4'-dihydroxydiphenyl sulfone, hydroquinone, 1,5-dihydroxynaphthalene, 2,7-dihydroxynaphthalene, 4,4'-biphenol, 4,4'-dihydroxybenzophenone, Bisphenol AF and Bisphenol A. Replacement of a portion of the dihalide compound with an equivalent amount of compound I (where n is 2) or end-capping the poly(ether sulfone) with a compound I (where n is 1) leads to a crosslinkable polymer composition according to this invention, having a co-repeat unit VIII or end-group IX, respectively. A method for the preparation of poly(arylene ether sulfones) which is adaptable to inclusion of units VIII or IX is disclosed in Johnson et al., U.S. Pat. No. 4,175,175 (1979), the disclosure of which is incorporated by reference.

Yet another class of polymers which can be crosslinked by the inclusion of co-repeat units VIII and/or end group IX is the poly(arylene ether ketones), exemplary preferred repeat units of which are XIIIa–g:

(XIIIa)

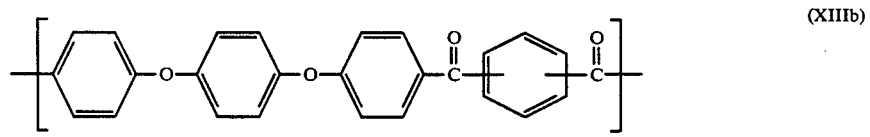

(XIIIb)

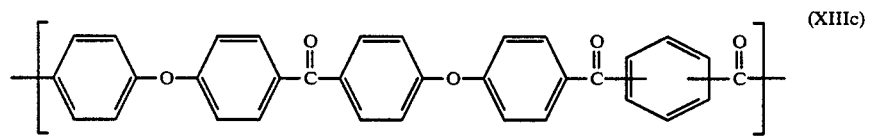

(XIIIc)

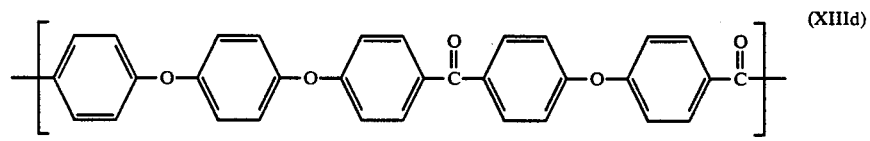

(XIIId)

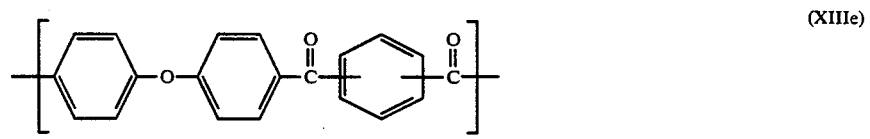

(XIIIe)

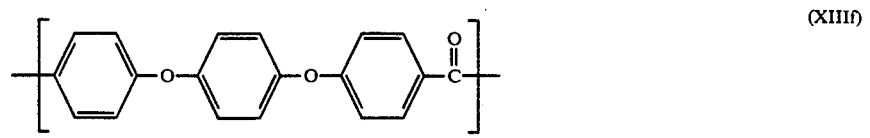

(XIIIf)

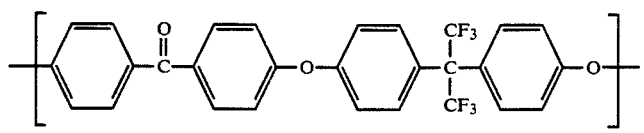

(XIIIg)

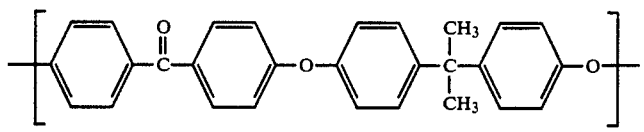

(XIIIh)

Poly(arylene ether ketones) can be made from the polymerization of a diphenol H-W-H with an activated dihalide compound, at least one of the diphenol and the dihalide compound having a ketone group. Suitable diphenols include hydroquinone, Bisphenol A, 4,4'-dihydroxybenzophenone, 1,5-dihydroxynaphthalene, 2,7-dihydroxynaphthalene, 4,4'-dihydroxydiphenylsulfone, 4,4'-biphenol, and Bisphenol AF. Suitable dihalide compounds include 4,4'-dihalobenzophenone and 4,4'-dihaloterephthalophenone, with the halogens being chlorine and more preferably fluorine. Methods for the preparation of poly(arylene ether ketones) which are readily adaptable to the inclusion of co-repeat units VIII and/or end groups IX are disclosed in Attwood et al., Polymer 22, 1096 (1981), and Rose et al., U.S. Pat. No. 4,320,224 (1982), the disclosures of which are incorporated herein by reference.

Polymer compositions crosslinked according to this invention can be used in a variety of electronic applications, including as dielectrics in multichip modules or multilayer electronic interconnects, as protective layers or coatings in electronic article packaging, or as substrates for printed circuit boards.

Films or coatings of the uncrosslinked compositions, especially in the case of fluorinated poly(arylene ethers) X, can be formed by solution techniques such as spraying, spin coating, or casting, with spin coating being preferred. Preferred solvents are 2-ethoxyethyl ether, cyclohexanone, DMF, DMAc, methyl isobutyl ketone, 2-methoxyethyl ether, 5-methyl-2-hexanone, γ-butyrolactone, and mixtures thereof. Typically the coating thickness is between about 3 to about 15μ. Thereafter, crosslinking can be effected by heating to a temperature above the decomposition temperature of the triazene group, typically between 300° and 400° C., optionally with a stepped or stagewise heating profile, typically for between about 15 and 90 minutes total time. For effective crosslinking and gel formation, the amount of co-repeat units VIII and/or end groups IX is preferably between about 2 and about 15 mole %, more preferably between about 2 and about 10 mole %.

Additives can be used to enhance or impart particular target properties, as is conventionally known in the polymer art, including stabilizers, flame retardants, pigments, plasticizers, surfactants, and the like. Compatible or non-compatible polymers can be blended in to give a desired property.

The practice of our invention can be further understood by reference to the following examples, which are provided by way of illustration and not of limitation. Those skilled in the art will appreciate the crosslinking groups VIII and IX can be incorporated into and used for crosslinking not just the fluorinated poly(arylene ethers), poly(arylene ether ketones), and poly(arylene ether sulfones), but other polymers which are adaptable to synthesis by nucleophilic displacement polymerization.

EXAMPLE 1

The preparation of hydrazides IV is illustrated by the following procedure for hydrazide IVd: To a 250 mL round bottom flask was added pyridine (100 mL) and 3-nitrobenzoic hydrazide (12.31 g, 0.0682 mol). To the mixture was added dropwise with stirring 2,6-difluorobenzoyl chloride (12.0 g, 0.0682 mol). The mixture was heated at reflux for 20 min and then allowed to cool to room temperature. Water was added to precipitate hydrazide IVd, which was then filtered, washed with water, and dried. Those skilled in the art will appreciate that this procedure is adaptable to the preparation of other hydrazides IV.

EXAMPLE 2

The preparation of oxadiazoles V is illustrated by the following procedure for oxadiazole Vd: Hydrazide IVd (17.0 g) was added to phosphorus oxychloride (72 g) in a 250 mL round bottom flask. The mixture was refluxed overnight under nitrogen. Most of the phosphorus oxychloride was then removed by distillation. The residue was poured into ice water to precipitate product Vd, which was isolated by filtration, washing with water, drying, and recrystallization from xylene. Its structure was confirmed by GC/MS. Those skilled in the art will appreciate that this procedure is adaptable to the preparation of other oxadiazoles V.

EXAMPLE 3

The following general procedure was used to preparation of amino oxadiazoles VI: To a solution of nitro oxadiazole V (15.0 g) in 150 mL of a tetrahydrofuran (THF):ethyl acetate:ethanol mixture (6:2:1 v:v:v) was added Pt/C catalyst (2.0 g, 0.5%). The resulting mixture was hydrogenated at 60 psi of hydrogen for 3 hr in a Parr hydrogenator. The catalyst was filtered off through a Celite filter pad and the solvent was removed under reduced pressure at about 35° C. The residue was dissolved in 300 mL THF and dried over anhydrous magnesium sulfate. Anhydrous hydrogen chloride was bubbled through the dried solution with mechanical stirring. The precipitate which formed was filtered, rinsed with anhydrous THF (100 mL), and dried in air and then vacuum to give amino oxadiazole VI as its hydrochloride, in 84–96% yield.

Results for representative amino oxadiazoles VI (or their hydrochlorides) are provided in Table II. $^1$H-NMR spectra in trifluoroacetic acid were consistent with the assigned structures.

TABLE II

| Amino oxadiazole VI (or Their Hydrochlorides) | | |
|---|---|---|
| Compound | Yield (%) | Melting Point (°C.) |
| VIa | 91 | 230 (dec)[a] |
| VIb | 84 | 225 (dec)[a] |
| VIc | 85 | 210 (dec)[a] |
| VIe | 96 | 215 (dec)[a] |
| VIf | 96 | 161-4[b] |
| VIj | 53 | 210 (dec)[a] |

[a]Hydrochloride
[b]Free base

EXAMPLE 4

A solution of concentrated hydrochloric acid (2.5 mL, 30.4 mmol) in water (50 mL) was added with mechanical stirring to a solution of difluoro amino oxadiazole VI (as hydrochloride, 5.00 g, 16.2 mmol) in THF (100 mL). The resulting solution was chilled to −2° C. A solution of sodium nitrite (1.40 g, 20.3 mmol) in water (40 mL) was added dropwise with stirring over a period of 20 min to the chilled solution while maintaining the temperature at −2° C. Stirring was continued for an additional 60 min at 0° C. A solution of dimethyl amine hydrochloride (5.00 g, 61.3 mmol) in water (25 mL) was added to the reaction mixture with vigorous stirring. The pH of the reaction mixture was then adjusted to 7 by the addition of 10% aqueous sodium carbonate. Stirring was continued for an additional 30 min. The organic solvent was removed under reduced pressure at about 35° C. The residue was filtered, rinsed with plenty of water, air dried, and vacuum dried at 40° C. overnight to give crude compound I, brownish in color. Crude compound I was chromatographed through activated basic alumina (300 g, packed in 50 mm ID glass column with n-hexane) using THF as the mobile phase. The first 500 mL of eluent were collected and the solvent was removed under reduced pressure at about 35° C. The residue was recrystallized from hexane/THF to give compound I. Those skilled in the art will appreciate that other compounds I, whether difluoro-, monochloro-, or dichloro-, can be similarly prepared, using different amino oxadiazoles VI and adjusting the stoichiometry accordingly.

Results for representative compounds I are provided in Table IIIa and IIIb.

TABLE IIIa

| | | Compounds I | | | |
|---|---|---|---|---|---|
| Compound | Melting Point (°C.) | $T_d$ (°C.)[a] | Yield (%) | Purity (%)[b] | $^1$H-NMR($\delta$(ppm)) (CDCl$_3$ solvent unless noted otherwise) |
| Ia | 185-7 | 244 | 85 | 95 | 3.24(s, 3H), 3.58(s, 3H), 7.32(m, 2H), 7.58(d, 2H), 8.08(d, 2H), 8.28 (m, 1H) |
| Ib | 128-30 | 244 | 84 | 98 | 3.21(s, 3H), 3.55(s, 3H), 7.22-7.36 (m, 2H), 7.40-7.61(m, 2H), 7.84(d, 1H), 8.07(s, 1H), 8.22(m, 1H)[c] |
| Ic | 167 | 245 | 70 | — | 3.38(d, 6H), 7.09(t, 2H), 7.42-7.52 (m, 1H), 7.54(d, 2H), 8.80(d, 2H) |
| Ie | 203-5 | 290 | 26 | 94 | 3.40(d, 6H), 7.21(d, 2H), 7.25(d, 2H), 7.56(d, 2H), 8.08(d, 2H), 8.14 (m, 4H) |
| If | 130-2 | 299 | 85 | 95 | 3.23(s, 3H), 3.58(s, 3H), 7.40(t, 2H), 7.56(m, 2H), 7.89(d, 1H), 8.12(s, 1H), 8.24(q, 2H) |
| Ig | 105[a] | 260 | 20 | — | 1.28(s, 6H), 3.79(q, 4H), 7.04(t, 2H), 7.44-7.53(m, 1H), 7.54(d, 2H), 8.08 (d, 2H) |
| Ih | 55[a] | 283 | 47 | — | 0.94(d, 6H), 1.36(m, 4H), 1.65(s, 4H), 3.70(t, 4H), 7.04(t, 4H), 7.45-7.53(m, 1H), 7.54(d, 2H), 8.08(d, 2H) |
| Ii | 142[a] | 259 | 18 | — | 3.40(s, 4H), 3.91(s, 4H), 4.93(s, 2H), 7.36(t, 2H), 7.50(d, 2H), 7.74(q, 1H), 7.99(d, 2H)[d] |
| Ij | 149-51 | 299 | 41 | >98 | 3.40(b, 6H), 7.27-7.60(m, 4H), 7.87 (d, 1H), 8.05-8.13(m, 3H) |

[a]By DSC at 10° C./min; $T_d$ = exothermic decomposition peak temperature
[b]By RP C-18 LC with 65% THF (aq.) as the mobile phase
[c]Acetone-d$_6$ solvent
[d]DMSO-d$_6$ solvent

TABLE IIIb

| | Elemental Analysis of Selected Compounds I | | | |
|---|---|---|---|---|
| Compound | Calculated(Found)(%) | | | |
| | C | H | F | N |
| Ic | 58.36 (58.69) | 3.98 (4.03) | 11.54 (11.23) | 21.27 (21.65) |
| Ig | 60.50 (60.35) | 4.79 (4.68) | 10.63 (10.41) | 19.60 (19.45) |
| Ih | 63.91 (63.79) | 6.09 (5.98) | 9.19 (not done) | 16.94 (16.77) |
| Ii | 55.53 (55.41) | 4.40 (4.63) | 9.76 (not done) | 17.99 (17.76) |

EXAMPLE 5

This example illustrates a first general procedure for the preparation of crosslinkable polymeric compositions having a co-repeat unit VIII or terminal group IX. This procedure is especially suitable for the preparation of fluorinated poly(arylene ethers) X.

Compound Ia (0.50 g, 0.0015 mol), bisphenol AF (4.08 g, 0.012 mol), potassium carbonate (4.2 g), and DMAc (35 g) were combined in a 100 mL round bottom flask. The mixture was heated at 120° C. under nitrogen and with stirring for 17 hr. After the mixture was allowed to cool to room temperature, decafluorobiphenyl (3.65 g, 0.011 mol; deliberate stoichiometric imbalance to control molecular weight) was added. The mixture was then re-heated with stirring and under nitrogen for another 2 hr. The mixture was allowed to cool to room temperature and poured into a blender containing water (200 mL) to precipitate the polymer. The polymer was isolated by filtration, washed with water, and dried to yield a white powder.

EXAMPLE 6

This example illustrates a second general procedure for the preparation of crosslinkable polymeric compositions having a co-repeat unit VIII or terminal group IX. This procedure is especially suitable for the preparation of polymers made from a diphenol and an aromatic dihalide in which the halogens are activated by electronegative substituents.

Compound Ia (1.00 g, 0.003 mol), Bisphenol A (3.42 g, 0.015 mol), 4,4'-dichlorodiphenylsulfone (3.44 g, 0.012 mol), potassium carbonate (5.0 g), and DMAc (30 g). The mixture was heated at 140° C. with stirring and under nitrogen for 24 hr, allowed to cool to room temperature, and poured into a blender containing water (about 200 mL) to precipitate the polymer. The polymer was isolated by filtration, washed with water, and dried to yield a white powder.

While in this and the foregoing example polymerizations have been described with reference to specific embodiments, those skilled in the art will appreciate that other crosslinking polymers can be made in accordance with the principles illustrated, mutatis mutandis.

EXAMPLE 7

This example provides a generally applicable procedure for the preparation of films of crosslinked polymer: A solution of triazene functionalized polymer (via units VIII or IX) at 15-25 wt % in a 50/50 mixture of cyclohexanone and γ-butyrolactone was spin coated on a glass substrate and dried for 10 min at 100° C. and 5 min at 150° C., and then ramped to 350° C. under nitrogen over 20 min, held at 350° C. for 30 min, cooled to 200° C. in about 30 min, and removed from the oven. The film was removed from the substrate by immersion in water. Gel contents for the cured films were determined by extraction with DMAc in a Soxhlet extractor for 17 hr. Results for various polymers are provided in Table IV.

TABLE IV

Curing of Polymer Samples

| Polymer | Repeat units and/ or end groups[a] | Gel content (%)[b] | Triazene $T_d$ (°C.)[c] | $T_g$ of cured film (°C.)[d] |
|---|---|---|---|---|
| XIV | A(1);B(7) | 97 | 301 | 205 |
| XV | C(1);B(7) | 95 | — | — |
| XVI | D(1);E(4.5);F(3) | 98 | 301 | 277 |
| XVII | D(1);E(7) | 98 | 303 | 293 |
| XVIII | G(1);E(7) | 94 | 302 | — |
| XIX | H(1);B(7) | 99 | — | 234 |
| XX | J(1);E(3) | 90 | — | — |
| XXI | K(1);L(4) | 93 | 309 | 190 |
| XXII | H(1);M(6) | 98 | 305 | 198 |
| XXIII | J(1);M(3) | 83 | 305 | 172 |
| XXIV | J(1);N(3) | 72 | 306 | — |
| XXV | O(1);N(3) | 73 | 301 | — |
| XXVI | O(1);P(6.5)[e] | 94 | 302 | — |

[a]Relative molar amounts indicated parenthetically
[b]Average of two or more runs
[c]Decomposition temperature peak by TGA
[d]Glass transition temperature by DSC
[e]Made using compound Ij The structures of the repeat units or end groups A-P are listed below:

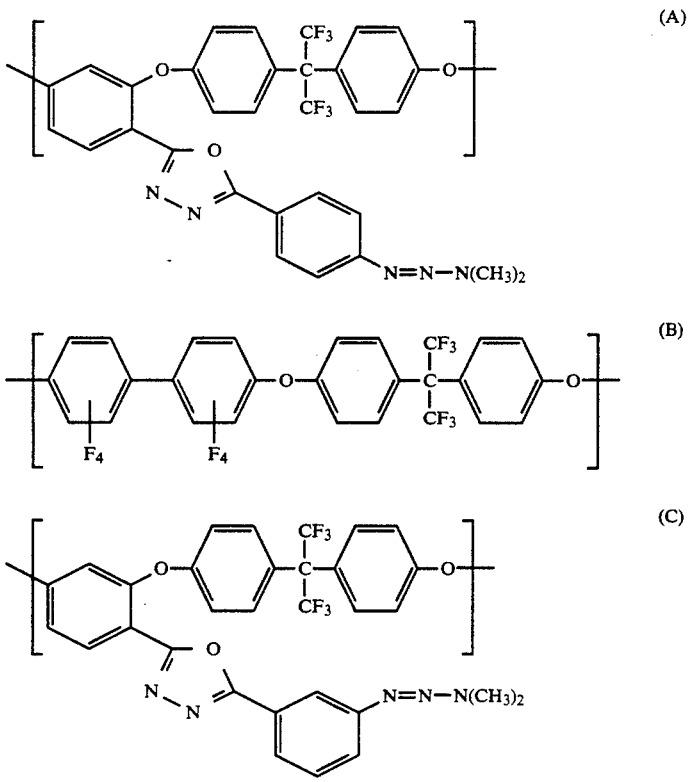

-continued
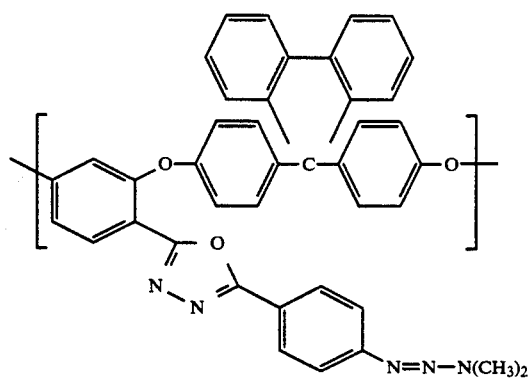
(D)
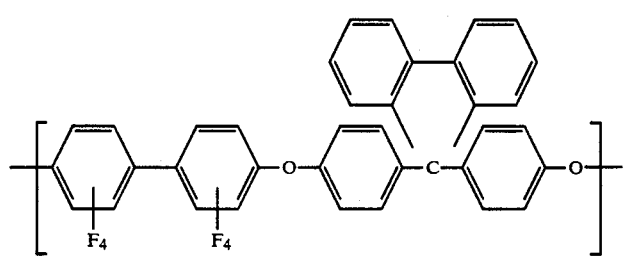
(E)
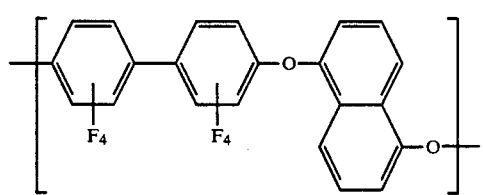
(F)
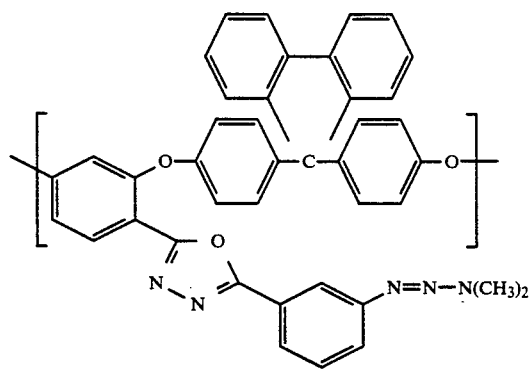
(G)
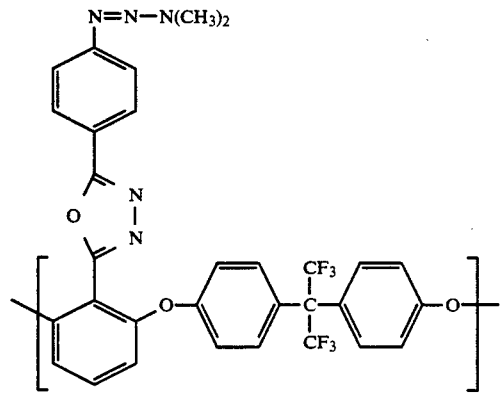
(H)

-continued

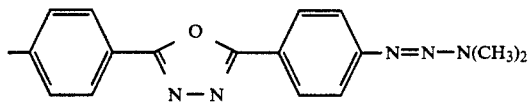
(J)

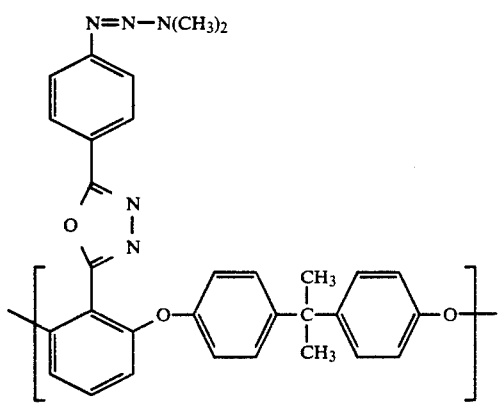
(K)

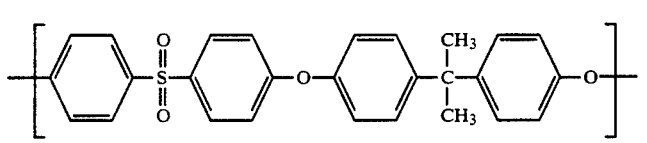
(L)

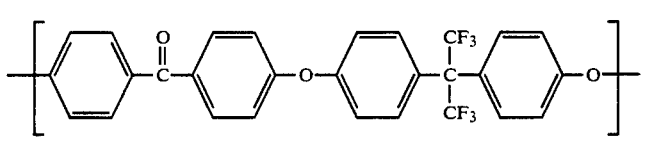
(M)

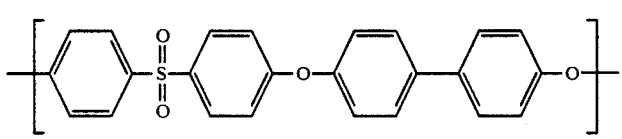
(N)

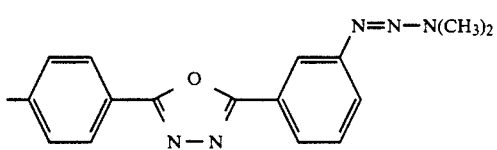
(O)

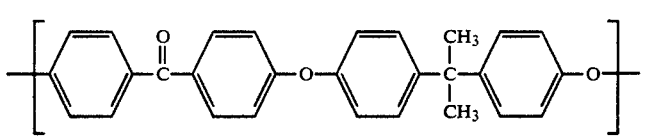
(P)

Molecular weight data for selected polymers (before crosslinking) are provided in Table V following.

TABLE V

Molecular Weight Data for Selected Polymers[a]

| Polymer | Number-average Molecular Weight ($M_n$) | Weight-average Molecular Weight ($M_w$) |
|---|---|---|
| XIV | 13,300 | 63,900 |
| XVI | 8,500 | 26,300 |
| XVII | 11,400 | 87,900 |
| XVIII | 9,300 | 36,000 |
| XIX | 11,000 | 29,200 |

[a]Polystyrene standards

What is claimed is:
1. A compound having the structure

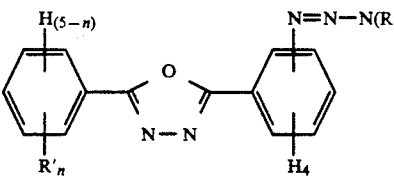

wherein —R' is —F or —Cl, each —R", which may be the same or different, is independently selected from the group consisting of $C_1$–$C_6$ alkyl or hydroxyalkyl moieties and aryl moieties, and n is 1 or 2.

2. A compound according to claim 1, wherein each —R" is the same and is selected from the group consisting of —CH₃, —CH₂CH₃, —CH₂CH₂CH₂CH₃, and —CH₂CH₂OH.

3. A compound according to claim 1, wherein n equals 2, —R' is —F and the —F's occupy the 2- and 4- positions.

4. A compound according to claim 3, wherein each —R" is —CH₃.

5. A compound according to claim 1, wherein n equals 2, —R' is —F and the —F's occupy the 2- and 6- positions.

6. A compound according to claim 5, wherein each —R" is —CH₃.

7. A compound according to claim 1, wherein n equals 1, —R' is —F, and the —F occupies the 4- position.

8. A compound according to claim 7, wherein each —R" is —CH₃.

9. A compound according to claim 1, wherein the triazene moiety —N=N—N(R")₂ occupies the 4'-position.

10. A compound according to claim 1, wherein the triazene moiety —N=N—N(R")₂ occupies the 3'-position.

11. A compound according to claim 1, wherein R' is —Cl.

12. A compound according to claim 1, selected from the group consisting of

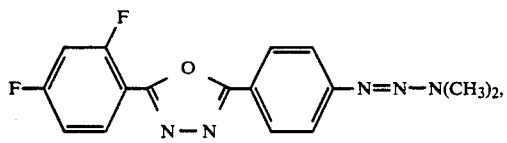

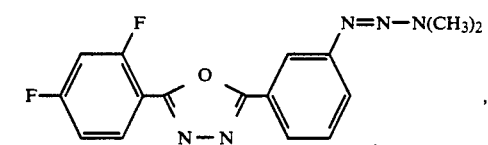

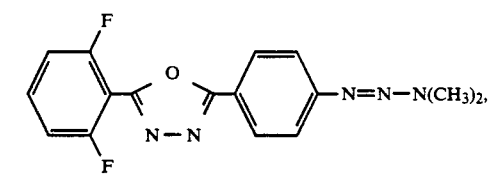

-continued

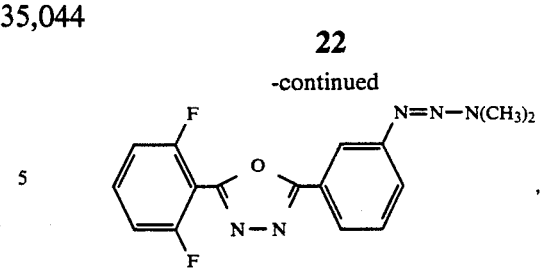

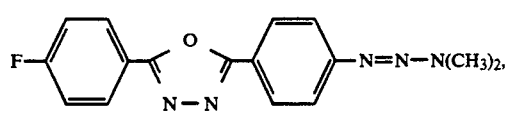

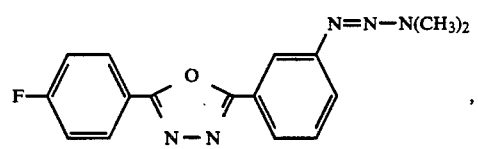

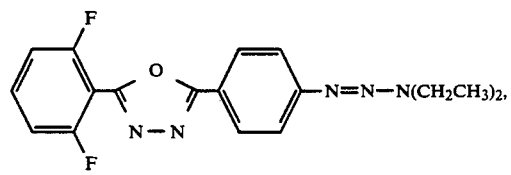

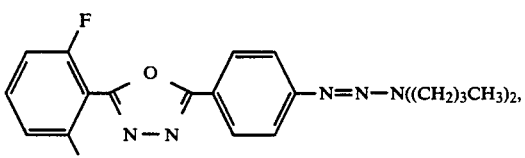

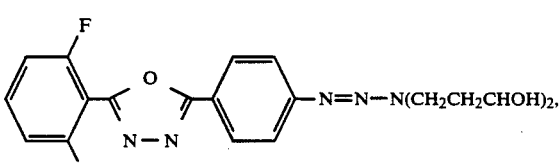

and

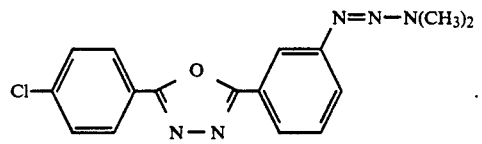

* * * * *